(12) United States Patent
Das et al.

(10) Patent No.: US 9,237,876 B2
(45) Date of Patent: Jan. 19, 2016

(54) SINGLE STEP X-RAY PHASE IMAGING

(71) Applicant: UNIVERSITY OF HOUSTON SYSTEM, Houston, TX (US)

(72) Inventors: Mini Das, Houston, TX (US); Doğa Gürsoy, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 94 days.

(21) Appl. No.: 14/032,276

(22) Filed: Sep. 20, 2013

(65) Prior Publication Data

US 2014/0079184 A1    Mar. 20, 2014

Related U.S. Application Data

(60) Provisional application No. 61/703,565, filed on Sep. 20, 2012.

(51) Int. Cl.
*G01N 23/04* (2006.01)
*A61B 6/00* (2006.01)
*A61B 8/08* (2006.01)

(52) U.S. Cl.
CPC .......... *A61B 6/484* (2013.01); *A61B 6/583* (2013.01); *A61B 8/085* (2013.03); *A61B 8/485* (2013.01)

(58) Field of Classification Search
CPC ....... G01N 23/00; G01N 23/02; G01N 23/04; G01N 23/06; G01N 23/083; G01N 23/087; A61B 6/482; A61B 6/484; A61B 6/5247

USPC ........................... 378/51, 53, 62, 63
See application file for complete search history.

(56) References Cited

U.S. PATENT DOCUMENTS

| | | | | |
|---|---|---|---|---|
| 6,163,590 | A  * | 12/2000 | Wilkins | 378/43 |
| 6,934,409 | B2 * | 8/2005 | Ohara | 382/132 |
| 2005/0228271 | A1* | 10/2005 | Diebold et al. | 600/425 |
| 2009/0238334 | A1 | 9/2009 | Brahme et al. | |
| 2010/0220832 | A1 | 9/2010 | Ning et al. | |
| 2010/0322380 | A1 | 12/2010 | Baeumer et al. | |
| 2012/0008747 | A1 | 1/2012 | Roessl et al. | |

OTHER PUBLICATIONS

M. Bech et al., "X-ray imaging with the PILATUS 100k detector," Applied Radiation and Isotopes, (2008), vol. 66, pp. 474-478.
PCT/US2013/060874 International Search Report and Written Opinion dated Jan. 8, 2014.

* cited by examiner

*Primary Examiner* — Jurie Yun
(74) *Attorney, Agent, or Firm* — Conley Rose, P.C.

(57) ABSTRACT

A system and method for single step x-ray phase contrast imaging. In one embodiment, a method for single step x-ray phase contrast imaging includes illuminating an object to be imaged with x-rays. The x-rays passing through the object are detected by a spectral detector. Image data derived from the detected x-rays is provided to an x-ray image processor. A phase image is generated based on the image data.

15 Claims, 3 Drawing Sheets

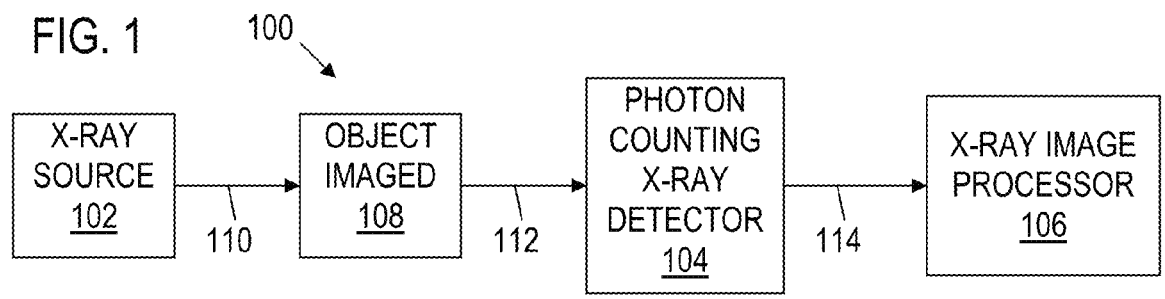
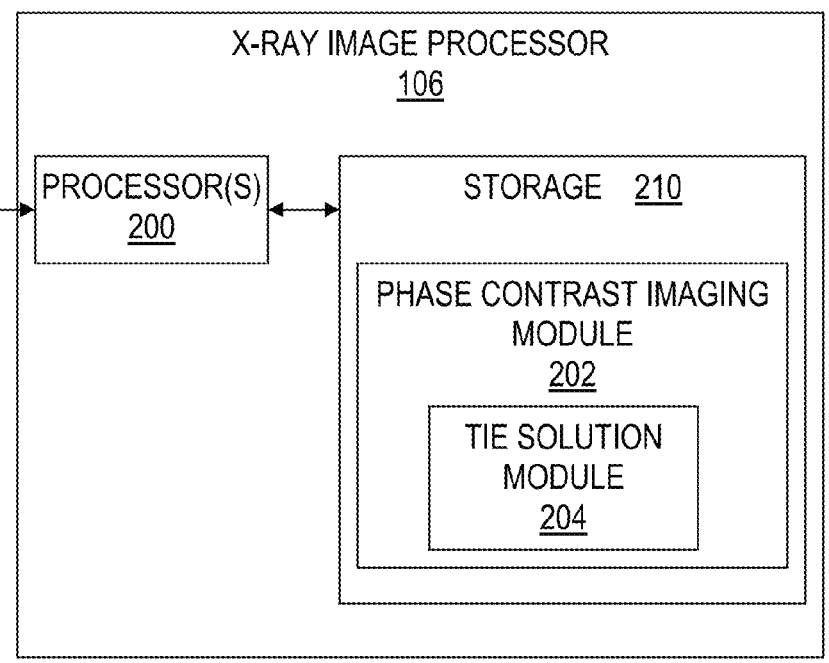

FIG. 3
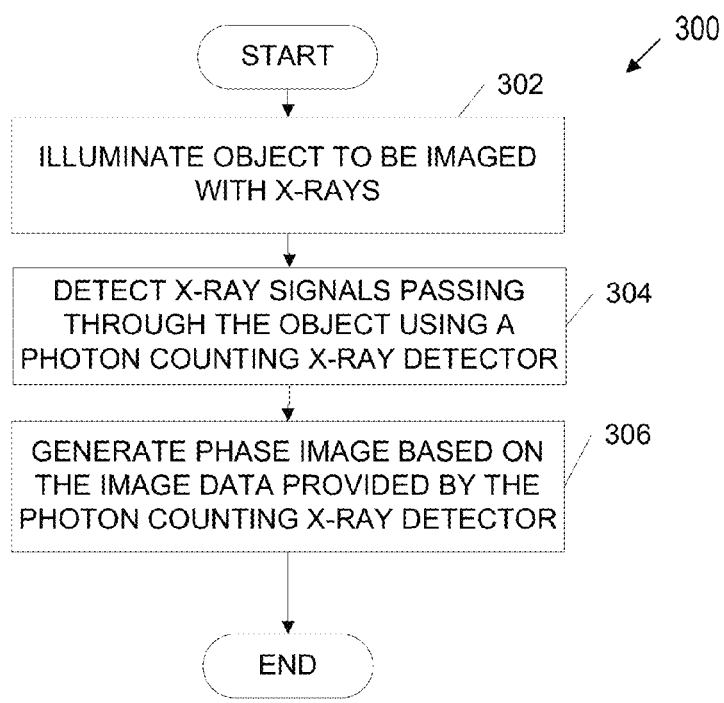
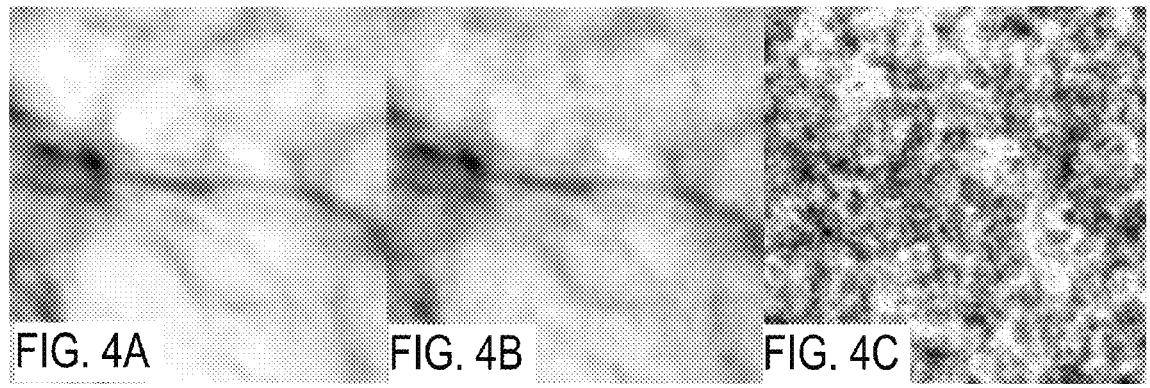
FIG. 4A  FIG. 4B  FIG. 4C
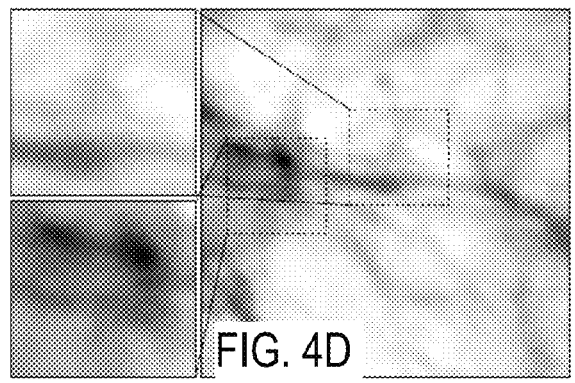
FIG. 4D

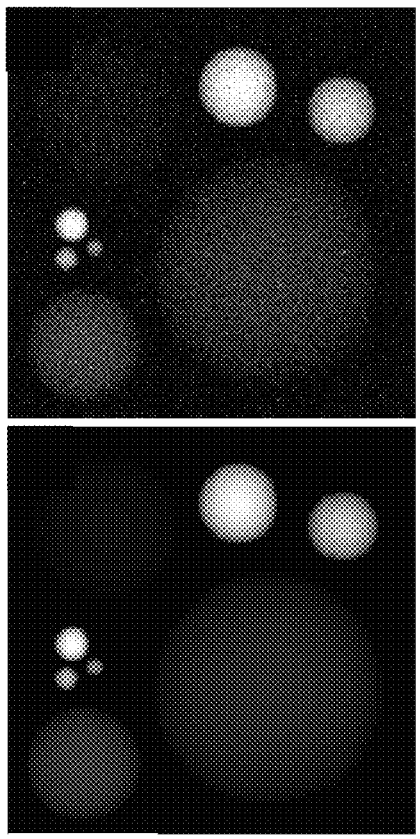
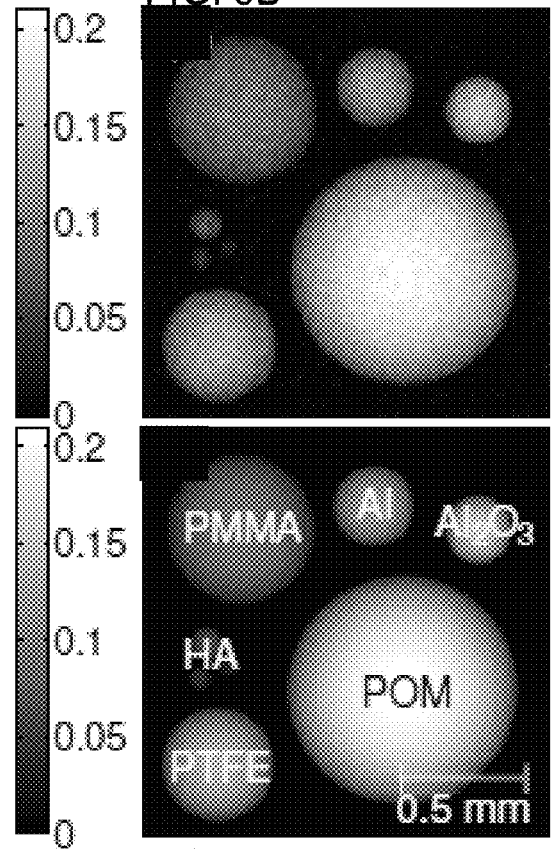
FIG. 5A  FIG. 5B
FIG. 5C  FIG. 5D
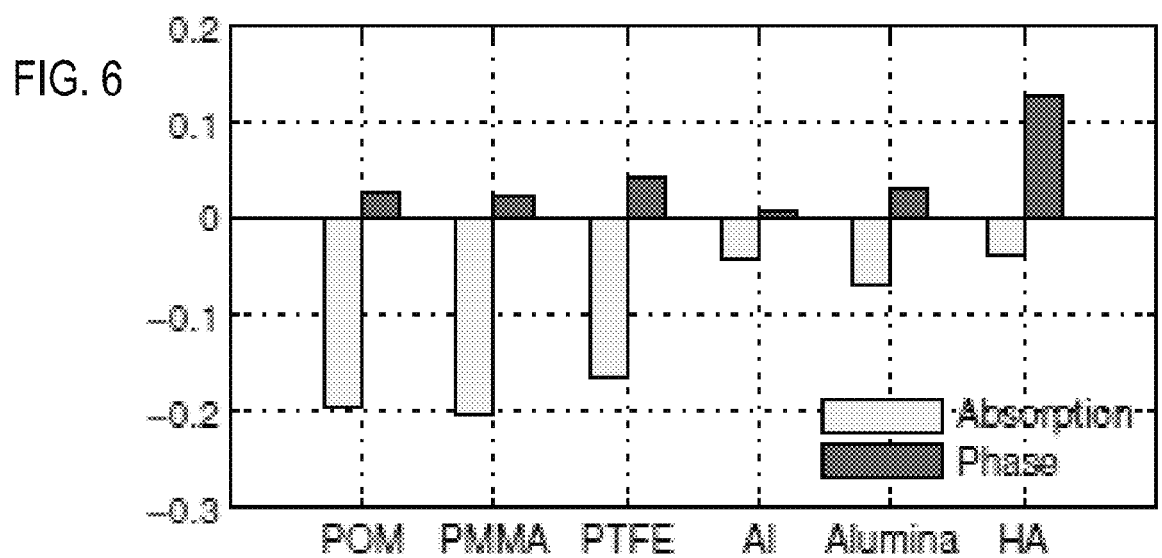
FIG. 6

SINGLE STEP X-RAY PHASE IMAGING

CROSS-REFERENCE TO RELATED APPLICATION

The present application claims priority to U.S. Provisional Patent Application No. 61/703,565, filed on Sep. 20, 2012, entitled "Single Step X-ray Phase Imaging," which is hereby incorporated herein by reference in its entirety.

BACKGROUND

The penetrative ability of x-rays makes them valuable for structural imaging applications ranging from medical imaging and materials research to quality control and security. Transmission imaging with x-rays is typically used to produce an attenuation contrast image of the material of interest. However, attenuation contrast images suffer from poor contrast sensitivity that poses severe limitations in many applications. The contrast sensitivity of transmission imaging is also an issue in medical imaging. Detection of early stage cancer (as represented by tumors smaller than 1 cm) is of vital importance. Transmission imaging is a workhorse imaging modality, yet is not sensitive enough to reliably detect such tumors.

SUMMARY

A system and method for single step x-ray imaging are disclosed herein. In one embodiment, a method for single step x-ray phase contrast imaging includes illuminating an object to be imaged with x-rays. The x-rays passing through the object are detected by a spectral detector. Image data derived from the detected x-rays is provided to an x-ray image processor. A phase image is generated based on the image data.

In another embodiment, a system for single step x-ray phase contrast imaging includes an x-ray source, a spectral detector, and an x-ray image processor. The spectral detector is configured to extract spectral data from x-rays produced by the x-ray source. The x-ray image processor is configured to generate a phase image of an object illuminated by the x-ray source based on x-ray data provided by the spectral detector.

In a further embodiment, an x-ray image processor includes a processor and a phase imaging module. The phase imaging module, when executed, causes the processor to generate a phase image representing an object illuminated by an x-ray source based on x-ray spectral data provided by a spectral detector. The x-ray spectral data includes a count of photons detected at each pixel of the spectral detector.

BRIEF DESCRIPTION OF THE DRAWINGS

For a detailed description of exemplary embodiments of the invention, reference will now be made to the accompanying drawings in which:

FIG. 1 shows a block diagram for a system for single step x-ray phase contrast imaging in accordance with principles disclosed herein;

FIG. 2 shows a block diagram for an x-ray image processor for single step x-ray phase contrast imaging in accordance with principles disclosed herein;

FIG. 3 shows a flow diagram for a method for single step x-ray phase contrast imaging in accordance with principles disclosed herein;

FIGS. 4A-4D show exemplary images illustrating single step x-ray phase imaging in accordance with principles disclosed herein;

FIGS. 5A-5D show exemplary absorption and phase images generated in accordance with principles disclosed herein; and FIG. 6 shows relative error in retrieved absorption and phase values for the phantom associated with images 5A-5D.

NOTATION AND NOMENCLATURE

In the following discussion and in the claims, the terms "including" and "comprising" are used in an open-ended fashion, and thus should be interpreted to mean "including, but not limited to . . . ." In addition, the term "couple" or "couples" is intended to mean either an indirect or a direct connection. Thus, if a first device couples to a second device, that connection may be through a direct connection, or through an indirect connection accomplished via other devices and connections. Further, the term "software" includes any executable code capable of running on a processor, regardless of the media used to store the software. Thus, code stored in memory (e.g., non-volatile memory), and sometimes referred to as "embedded firmware," is included within the definition of software. The recitation "based on" is intended to mean "based at least in part on." Therefore, if X is based on Y, X may be based on Y and any number of other factors.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The limited contrast sensitivity of attenuation contrast (AC) images is problematic in breast cancer screening and other x-ray applications. In digital mammography (DM) and digital breast tomosynthesis (DBT), radiologists must typically rely on structural artifacts and architectural distortions that appear in the images to diagnose malignant breast masses. For example, architectural distortion in the cancerous tissue may be the only way to identify malignancy.

As electromagnetic waves, x-rays propagating through tissue undergo phase change $\phi$ as well as attenuation. The magnitude of the phase change is determined by the imaginary part of the tissue's complex refractive index:

$$n = 1 - \delta + i\beta. \tag{1}$$

The imaginary part $\beta$ is related to the linear absorption coefficient $\mu(E)$ through the equation:

$$\mu(E) = 4\pi\beta/\lambda. \tag{2}$$

The real part ($\delta$) is:

$$\delta(E) = (\lambda^2 r_e \rho_e)/2\pi \tag{3}$$

where:
$r_e$ is the classical electron radius,
$\lambda$ is the wavelength associated with energy E, and
$\rho_e$ is the electron density (ED) in the tissue.

If $\delta$ is a function of location (x, y, z), the phase change (retardation) is:

$$\phi(x, y; z, \lambda) = -\frac{2\pi}{\lambda} \int \delta(x, y, z'; \lambda) dz', \quad (4)$$

where the optic axis is assumed to be parallel to z. In accordance with equation (3), phase changes are directly linked to electron density variations in the tissue. With x-ray energies between 10 and 100 keV, phase changes in soft tissue may be 1000 times higher than attenuation changes. Phase-contrast imaging refers to techniques for mapping the changes in phase, either by estimating φ directly or by estimating the gradient ∇φ or the Laplacian ∇²φ if there is insufficient contrast in φ alone.

A polychromatic source with a high spatial coherence such as a microfocus x-ray source can be used for phase imaging. While interferometric methods have been implemented in a laboratory setting, such methods require precise measurements and are experimentally cumbersome. The in-line phase contrast imaging (ILPC) method, while being the simplest of these techniques, still requires multiple measurements to retrieve a single phase projection. This is due to the difficulty in extracting phase from a single intensity measurement (the well known "phase problem" in optics).

Embodiments of the present disclosure (systems and methods) apply novel techniques that increase the contrast sensitivity for x-ray based soft tissue imaging. Embodiments provide improved and practical phase retrieval using photon counting detector technology, which yields both temporal and energy discrimination of photons, for x-ray detection. Using the photon counting detector (PCD), embodiments provide a single step measurement that simultaneously yields intensity measurements corresponding to photons of multiple energy levels thereby providing a novel solution to the phase problem. The single-step (i.e., single acquisition) phase retrieval techniques disclosed herein acquire spectral data at a single distance, far enough from the subject to record the phase changes in the wave. An estimate of the projected ED map is then obtained through a solution of the relevant transport of intensity equations (TIEs). An exact measure of the ED map can be obtained by converting the acquisition to tomography. The single-step phase contrast imaging disclosed herein substantially reduces the dose of radiation delivered to the subject while enhancing visibility of low contrast structures. In contrast to conventional methods, the single-step phase retrieval method of the present disclosure puts no constraints on x-ray imaging energy, tissue composition, or absorption properties.

Embodiments of the x-ray system disclosed herein are applicable to soft tissue imaging like breast imaging and prostate imaging, x-ray imaging of luggage in baggage claims, detection of explosives using x-ray imaging, and other x-ray imaging applications. Embodiments are also applicable to materials science and studies where an electron density map of thick objects is required, and has applications in all phase retrieval methods using x-rays or other electromagnetic radiation.

FIG. 1 shows a block diagram of a system 100 for single step x-ray phase contrast imaging in accordance with various embodiments. The system 100 includes an x-ray source 102, a photon counting x-ray detector (PCD) 104, and an x-ray image processor 106. The x-ray source 102 may be a polychromatic source with a high spatial coherence such as a microfocus x-ray source (e.g., 10s of microns).

While embodiments may apply various photon counting x-ray detectors as the PCD 104, some embodiments apply Medipix (MED) detectors. Medipix detectors are photon-counting pixel detectors originally devised for astrophysical applications, and include a semiconductor sensor layer bonded to an electronics layer. The semiconductor layer is based on semiconductor material such as Si, CdTe, CdZTe and/or GaAs that generates an electron/hole cloud when radiation is incident thereon. The electronics count the number of events in each pixel (e.g., 256×256 pixels or more). The energy of each counted photon is compared to thresholds (which may be variably set) allowing for energy/wavelength discrimination. Some MED detectors can record the detection time and the energy of every detected photon (i.e., a timpix detector). Additionally, such detectors offer extremely low noise, high resolution (50 micron pixel size) and a large dynamic range.

The x-ray image data 114, including amplitude, pixel event count, energy and/or time of detection of each photon, produced by the PCD 104 is transferred to the x-ray image processor 106. The x-ray image processor 106 processes the x-ray image data to generate a phase contrast image of the subject 108 illuminated by the x-rays.

Conventional methods for extracting phase information from a single intensity measurement can require approximations about absorption property of the object and sometimes require prior knowledge about the object which has hindered their practical application. Consequently, conventional ILPC imaging techniques that use a polychromatic x-ray source and energy integrating detectors employ multiple measurement steps. In contrast, embodiments disclosed herein use the additional information obtained using the PCD 104 to enable phase extraction in a single step using a novel phase retrieval technique. The PCD 104 acquires at least two energy windows per projection angle.

The x-ray image processor 106 performs the quantitative recovery of phase in ILPC as disclosed herein by processing the image data provided by the PCD 104 to solve a Transport of Intensity Equation (TIE). TIE describes a functional relationship between the evolution of intensity distribution in cross section of the x-ray beam and the shape of its beam wavefront. When illuminating the object 108 with the partially coherent, polychromatic cone-beam x-ray source 102, according to TIE, the measured intensity at distance $R_2$ from the object-plane is:

$$I_{R_2}(E) = \frac{I_0(E)}{M^2}\left(I_{R_1}(E) + \frac{R_2}{kM}\nabla I_{R_1}(E)\nabla\varphi(E)\right) \quad (5)$$

where:
$I_{R_1}(E)$ is the intensity of the x-ray wave at the object plane;
$I_0(E)$ is the incident x-ray intensity;
$M=R_2/(R_1+R_2)$ is the magnification factor resulting from the cone beam geometry;
$R_1$ and $R_2$ represent the distances of the source-to-object and object-to-detector; and
φ(E) is the phase change of the x-ray as it propagates through medium and is proportional with the Radon transform of the refractive index decrement of the object.

The TIE can be simplified as follows by using either Rytov or Born approximation:

$$I_{R_2}(E) = \quad (6)$$

-continued $$\frac{I_0(E)}{M^2}I_{R_1}(E)\left(1+\frac{R_2}{kM}\nabla^2\varphi(E)\right) = \frac{I_0(E)}{M^2}I_{R_1}(E)\exp\left(\frac{R_2}{kM}\nabla^2\varphi(E)\right).$$

$I_{R_1}(E)$ is indirectly related to the phase because the attenuation is caused by not only the absorption but also the scattering of the x-rays which lead to refraction and in turn cause phase changes. Thus, $I_{R_1}(E)$ can be decomposed into absorption and scattering components to obtain a closed-form solution for the phase. Embodiments of the x-ray image processor 106 apply such an attenuation-partition based approach to the phase-retrieval problem to obtain the phase function.

In the energy ranges applied to image some objects (e.g., tissues, such as breast tissue), the photoelectric absorption and Compton scattering are the predominant modes of attenuation. Accordingly, embodiments approximate the attenuation as a linear combination of these energy dependent functions as follows:

$$\mu(E) = \rho\sigma_{KN}(E) + \rho\sigma_{PE}(E), \quad (7)$$

where:
ρ is the electron density; and
$\rho\sigma_{KN}(E)$ and $\rho\sigma_{PE}(E)$ are the electronic cross-sections for the Compton scattering and for the photoelectric emission.

The electron density (ρ) variations in the object 108 lead to refractive index changes and is hence related to the phase of the x-ray wave with the following linear relationship:

$$\phi(E) = -\frac{2\pi r_e}{k}\int \rho dz, \quad (8)$$

where k is the wave vector. Note that for the aforementioned x-ray energies, the dependence of electron density on the energy is very small and can be neglected. Therefore, embodiments may formulate the phase-retrieval problem in terms of the electron density when spectral measurements are used. Rearrangement produces the following linear expression:

$$-\ln\left(M^2\frac{I(E)}{I_0(E)}\right) = \left(\frac{K}{\xi^3(E)}\right)\int \rho Z_{eff}^4 dx + \left(\sigma_{KN}(E) - \frac{2\pi R_2 r_e}{k^2 M}\nabla^2\right)\int \rho dx. \quad (9)$$

Expression 9 is a linear equation of the form: $a_0(E) = a_1(E) b_1 + a_2(E) b_2$. Embodiments of the x-ray image processor 106 evaluate the Laplacian operator on the right hand side in the Fourier domain using a fast-Fourier transform. Embodiments may use two measurements at $E_1$ and $E_2$ (for example, 30 keV and 60 keV) to obtain two independent equations and use Gaussian elimination for the solution. After the Fourier transforms are estimated, the x-ray image processor 106 may obtain the projected electron density ($\int \rho dx$) using the inverse Fourier transform. Embodiments, produce the phase (φ) and the differential phase contrast (DPC) ($\nabla\phi$) from the obtained electron density projection.

Some embodiments of the system 100 apply a high frequency ultrasound (US) beam as a means to improve "phase contrast". For example, a malignant tumor may have 5-28 times more elasticity (or stiffness) than the normal background. Force of acoustic radiation can cause displacement in soft tissue depending on its density and act as an external contrast agent for phase contrast imaging. In combination with in line spectral phase retrieval using PCDs, ultrasound enables discrimination of malignancies from their surrounding by their elastic properties and density difference as small as few percent. Spectral phase detection using an external contrast agent is useful in further discriminating the types of malignancy (as an example aggressive vs. slow growing tumors).

FIG. 2 shows a block diagram for the x-ray image processor 106 for single step x-ray phase contrast imaging in accordance with various embodiments. The embodiment of the condition monitor 128 shown in FIG. 2 includes processor(s) 200 and storage 210 coupled to the processor(s) 200. The processor(s) 200 is an instruction execution device that executes instructions retrieved from the storage 210. Processors suitable for use as the processor(s) 200 may include general-purpose microprocessors, digital signal processors, microcontrollers, or other devices capable of executing instructions retrieved from a computer-readable storage medium. Processor architectures generally include execution units (e.g., fixed point, floating point, integer, etc.), storage (e.g., registers, memory, etc.), instruction decoding, peripherals (e.g., interrupt controllers, timers, direct memory access controllers, etc.), input/output systems (e.g., serial ports, parallel ports, etc.) and various other components and sub-systems.

The storage 210 is a non-transitory computer-readable storage medium suitable for storing instructions executable by the processor(s) 500. The storage 210 may include volatile storage such as random access memory, non-volatile storage (e.g., a hard drive, an optical storage device (e.g., CD or DVD), FLASH storage, read-only-memory), or combinations thereof. The storage 210 contains a phase contrast imaging module 202. The phase contrast imaging module 202 includes instructions that when executed by the processor(s) 200 cause the processor(s) 200 to generate phase images and/or phase contrast images based on image data provided by the photon counting x-ray detector 104 as disclosed herein. The phase contrast imaging module 202 includes a TIE solution module 204 that includes instructions for solving TIE as disclosed herein. Some embodiments of the x-ray image processor 106 may be implemented as a computer such as a desktop computer, a server computer, an array of computers, etc.

FIG. 3 shows a flow diagram for a method 300 for single step x-ray phase contrast imaging in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of the method 300, as well as other operations described herein, can be implemented as instructions stored in computer readable medium 210 and executed by the processor(s) 200.

In block 302, the x-ray source 102 generates an x-ray beam that illuminates the object 108 to be imaged. The x-ray beam may be a partially coherent, polychromatic cone-beam.

In block 304, the x-rays passing through the object 108 are detected by the photon counting x-ray detector 104. For each photon detected by the PCD 104, the time of detection, energy level, and per pixel count may be determined and recorded.

In block 306, the PCD 104 provides the x-ray data, including amplitude, energy level, detection time, count per pixel, etc. to the x-ray image processor 106. The x-ray image processor 106 processes the x-ray data provided by the PCD 104 to generate a phase image and/or a phase contrast image of the object 104. The x-ray image processor 106 processes the x-ray data in accordance with the operations (e.g., TIE solution operations) disclosed herein.

FIGS. 4A-4D show exemplary images illustrating single step x-ray phase imaging in accordance with principles disclosed herein. FIGS. 4A-4E were generated using realistic breast phantoms with embedded lesions. FIG. 4A shows a true phase image of the phantom. FIG. 4B shows a retrieved phase image of the phantom in accordance with the single step x-ray phase imaging technique disclosed herein. FIG. 4C shows relative error between the true (4A) and retrieved (4B) images to be less than 0.1% throughout the medium and uniformly distributed. FIG. 4D shows a digital mammography image of the phantom. The zoomed areas show the lesions.

FIGS. 5A-5D show exemplary absorption and phase images generated in accordance with principles disclosed herein. The phantom imaged in FIGS. 5A-5D includes six different materials: aluminum (Al), alumina ($Al_2O_3$), hydroxylapatite (HA), polytetrauoroethylene (PTFE), polyoxymethylene (POM) and polymethylmethacrylate (PMMA). The respective diameters of the materials are 0.14, 0.12, 0.03, 0.06, 0.2, 0.4 and 0.27 mm. Al, $Al_2O_3$, and HA represent strongly absorbing materials, and PTFE, POM, and PMMA represent weakly absorbing materials. FIGS. 5C and 5D respectively show the true absorption and phase images of the phantom at 35 keV. FIGS. 5A and 5B respectively show absorption and phase images of the phantom at 35 keV generated by x-ray imaging as disclosed herein.

FIG. 6 shows relative error in generated absorption and phase values for the phantom associated with images 5A-5D. For each material, error in the generated value is calculated with respect to the true value $$\left( e.g., \delta x = 1 - \frac{x_{ret}}{x_{true}} \right).$$

In FIG. 6, the relative errors shown for each material are averaged over the circular region associated with material. For additional information see Doğa Gürsoy & Mini Das, *Single-step absorption and phase retrieval with polychromatic x rays using a spectral detector*, OPTIC LETTERS, Vol. 38, Issue 9, 1461-63 (2013), which is hereby incorporated herein by reference in its entirety.

The above discussion is meant to be illustrative of the principles and various embodiments of the present invention. Numerous variations and modifications will become apparent to those skilled in the art once the above disclosure is fully appreciated. For example, while embodiments have been described with regard to a photon counting x-ray detector, those skilled in the art will understand that embodiments may employ other spectral detectors. It is intended that the following claims be interpreted to embrace all such variations and modifications.

What is claimed is:

1. A method for single step x-ray phase contrast imaging, comprising:
    illuminating an object to be imaged with x-rays;
    detecting, by a spectral detector, the x-rays passing through the object;
    providing image data derived from the detected x-rays to an x-ray image processor;
    processing the image data to decompose x-ray intensity into absorption and phase components using a Transport of Intensity Equation arranged to include electronic cross-sections for Compton scattering and photo-electric emission; and
    generating a phase image based on the image data.

2. The method of claim 1, wherein the detecting comprises counting a number of x-ray photons detected at each pixel of the spectral detector.

3. The method of claim 1, further comprising generating the x-rays using a micro-focus x-ray source.

4. The method of claim 1, wherein the generating comprises producing the phase image from a single x-ray illumination of the object.

5. The method of claim 1, further comprising generating an absorption image based on the image data.

6. The method of claim 1, wherein the image data comprises a count of detected photons per pixel and an energy value per pixel.

7. The method of claim 1, further comprising enhancing phase contrast in the object by applying an ultrasound beam to the object.

8. A system for single step x-ray phase contrast imaging, comprising:
    an x-ray source;
    a spectral detector configured to extract spectral data from x-rays produced by the x-ray source;
    an x-ray image processor configured to:
        process the spectral data to decompose x-ray intensity into absorption and phase components using a Transport of Intensity Equation arranged to include electronic cross-sections for Compton scattering and photo-electric emission; and
        generate a phase image of an object illuminated by the x-ray source based on the spectral data.

9. The system of claim 8, wherein the spectral detector is a photon counting x-ray detector configured to count a number of x-ray photons detected at each pixel of the spectral detector.

10. The system of claim 8, wherein the x-ray source comprises a micro-focus x-ray generator.

11. The system of claim 8, wherein the x-ray image processor is configured to generate the phase image based on the spectral data acquired by the spectral detector during a single x-ray illumination of the object.

12. The system of claim 8, wherein the x-ray image processor is configured to generate an absorption image of the object based on the spectral data used to generate the phase image.

13. The system of claim 8, further comprising an ultrasound source configured to direct ultrasound signals onto the object while the object is illuminated by the x-rays, wherein the ultrasound signals enhance phase contrast in the object.

14. An x-ray image processor, comprising:
    a processor; and
    a phase imaging module that when executed causes the processor to:
        process x-ray spectral data, generated by a spectral detector responsive to illumination of an object by an x-ray source, to decompose x-ray intensity into absorption and phase components using a Transport of Intensity Equation arranged to include electronic cross-sections for Compton scattering and photo-electric emission; and
        generate a phase image representing the object based on the x-ray spectral data;
        wherein the x-ray spectral data comprises a count of photons detected at each pixel of the spectral detector.

15. The x-ray image processor of claim 14, wherein the phase imaging module causes the processor to generate the phase image based on spectral data produced from a single x-ray illumination of the object.

* * * * *